(12) United States Patent  
Gratwohl et al.

(10) Patent No.: US 8,647,307 B2  
(45) Date of Patent: Feb. 11, 2014

(54) NEEDLE PROTECTION DEVICE WITH A BLOCKED PROTECTIVE POSITION

(75) Inventors: Christian Gratwohl, Aarau (CH); Martin Wymann, Liebefeld (CH)

(73) Assignee: TecPharma Licensing AG, Burgdorf (CH)

( * ) Notice: Subject to any disclaimer, the term of this patent is extended or adjusted under 35 U.S.C. 154(b) by 792 days.

(21) Appl. No.: 12/399,712

(22) Filed: Mar. 6, 2009

(65) Prior Publication Data

US 2009/0221972 A1  Sep. 3, 2009

Related U.S. Application Data

(63) Continuation of application No. PCT/CH2007/000413, filed on Aug. 22, 2007.

(30) Foreign Application Priority Data

Sep. 6, 2006  (DE) .......................... 10 2006 042 236

(51) Int. Cl.  
*A61M 5/32* (2006.01)  
*A61M 5/00* (2006.01)

(52) U.S. Cl.  
USPC ........... 604/198; 604/192; 604/163; 604/171; 604/110

(58) Field of Classification Search  
USPC ........................... 604/110, 192, 198, 163, 171  
See application file for complete search history.

(56) References Cited

U.S. PATENT DOCUMENTS 6,773,415 B2 * 8/2004 Heiniger ........................ 604/110

FOREIGN PATENT DOCUMENTS

| EP | 1464353 A1 | 10/2004 |
| EP | 1557191 A2 | 7/2005 |
| FR | 2881053 A1 | 7/2006 |
| WO | 01/91837 A1 | 12/2001 |
| WO | 02/20074 A1 | 3/2002 |
| WO | 2004/000397 A1 | 12/2003 |

* cited by examiner

*Primary Examiner* — Kevin C Sirmons  
*Assistant Examiner* — Bradley G Thomas, Jr.  
(74) *Attorney, Agent, or Firm* — Dorsey & Whitney LLP; David E. Bruhn, Esq.

(57) ABSTRACT

A needle protection device including a needle holder for operable coupling to an injection device and from which an injection needle projects, a blocking device which projects from the needle holder and is radially distanced from the injection needle, a needle protection element which can be moved into a first position and, from the first position, to a protection position in which it surrounds the injection needle, and which can be blocked from leaving the protection position by the blocking device, and a safety member arranged between the injection needle and the needle protection element in such a way that it can be displaced in relation to the injection needle, wherein the needle protection element includes an engagement element and the safety member includes a counter-element, the engagement element and counter-element mutually engaging when the needle protection element is moved into the first position, the needle protection element thereby entraining the safety member during movement of the needle protection element into the protection position.

18 Claims, 4 Drawing Sheets

NEEDLE PROTECTION DEVICE WITH A BLOCKED PROTECTIVE POSITION

CROSS-REFERENCED RELATED APPLICATIONS

This application is a continuation of International Patent Application No. PCT/CH2007/000413 filed Aug. 22, 2007, which claims priority to German Patent Application No. DE 10 2006 042 236.8 filed Sep. 6, 2006, the entire contents of both of which are incorporated herein by reference.

BACKGROUND

The present invention relates to devices for injecting, delivering, infusing, dispensing or administering a substance, and to methods of making and using such devices. More particularly, it relates to a needle guard device which is or can be attached to an injection device of a type which may be used for administering or self-administering medicaments, for example insulin. The injection device may be a simple syringe or a syringe which is disposed of once it has been used. In such applications, the needle guard may be manufactured separately from the injection device and connected to the injection device in readiness for administering, or it may be an integrated part of the injection device and be disposed of with it. The injection device may be designed for repeated use and to enable a dose to be set or selected for the product to be administered. In some embodiments, the injection device may be an injection pen of the type used to treat diabetes and, these days, for other treatments as well.

When handling injection devices, there is a risk that patients or medical staff could be injured by an injection needle and/or be infected by an accidental stick by an injection needle that has already been used. With a view to preventing this, needle guard devices with a displaceable needle guard have been developed. For the injection, the injection device fitted with the needle guard device is pushed against the skin via the needle guard. Due to the pressure, the injection device, with the injection needle projecting from it in the distal (forward, front or injection) direction, moves in the distal direction relative to the needle guard so that the injection needle pierces the skin. Accordingly, the needle guard effects a movement in the proximal direction (rearwardly) relative to the injection device as far as a releasing position in which the injection needle projects in the distal direction beyond the needle guard by its injection portion which pierces the skin. When the injection needle is pulled back out of the skin, the needle guard is subjected to an elastic force of a rebounding element and moves in the distal direction again as far as a guard position in which it extends beyond the injection needle, including the needle tip. On reaching the guard position, the needle guard locks automatically so that it can not move back in the proximal direction relative to the injection needle again.

U.S. Pat. No. 6,773,415 B2 discloses such a needle guard device, which comprises an injection needle, a needle holder and a needle guard. The needle guard surrounds the needle holder and is mounted on it so that it can move axially. A locking element which is able to move axially is accommodated in the needle guard which is blocked on the needle holder when the needle guard is in the releasing position and is blocked on the needle guard when the injection needle is pulled out so that the needle guard is axially secured relative to the needle holder by the locking element after the injection. Since the locking element is blocked on both the needle holder and the needle guard and must also ensure a clean axial guiding action in sliding contact with the needle guard, it has a complex shape. The needle holder must also be of a specific shape to guide and hold the needle guard on the one hand and to lock the locking element axially on the other hand. The rebounding member must also be axially guided by the locking element and must therefore be relatively slim.

A needle guard device which can be attached to an injection device incorporating an injection needle is described in patent specification WO 01/91837 A1, for example. The device comprises a needle holder with an injection needle extending in the distal direction and a needle guard, which is mounted on the needle holder so that it can be moved out of a proximal position against the force of a return element into the releasing position and back out of the releasing position. The needle holder forms a branched guide track and the needle guard forms a locating element which is guided along the guide track. During an injection, the locating element moves through the two branches of the guide track one after the other and latches on the end of one branch of the guide track when the injection needle is pulled out so that the needle guard is blocked to prevent it from moving in the proximal direction again. This needle guard device also requires a needle holder with a complex shape. In addition, there is no guaranteeing that the catch connection defining the guard position will not be inadvertently released to the desired degree of reliability because the locating element is elastically bent several times before latching and may therefore project outwardly.

SUMMARY

An object of the present invention is to provide a needle guard device which is easy to manufacture and which reliably protects a user against contact with an injection needle after an injection.

In one embodiment, the present invention comprises a needle protection device comprising a needle holder for operable coupling to an injection device and from which a needle projects, a blocking device which projects from the needle holder and is radially distanced from the needle, a needle protection element which can be moved into a first position and, from the first position, to a protection position in which it surrounds the needle, and which can be blocked from leaving the protection position by the blocking device, and a safety member arranged between the needle and the needle protection element in such a way that it can be displaced in relation to the needle, wherein the needle protection element comprises an engagement element and the safety member comprises a counter-element, the engagement and counter-element mutually engaging when the needle protection element is moved into the first position, the needle protection element thereby entraining the safety member during movement of the needle protection element into the protection position.

In one embodiment, the present invention comprises a needle protector comprising a needle holder for operable coupling to an injection device and from which a needle projects, a lock which projects from the needle holder and is radially distanced from the needle, a needle protector or cover which can be moved into a first position and, from the first position, to a protecting position in which it surrounds the needle, and which can be prevented from leaving the protecting position by the lock, and a safety member arranged between the needle and the needle protector such that it can be displaced in relation to the needle, wherein the needle protector comprises an engagement element and the safety member comprises a counter-element, the engagement element and counter-element mutually engaging when the needle protector is moved into the first position, the needle protector thereby entraining the safety member during movement of the needle protector to the protecting position.

In some embodiments, the present invention comprises a needle guard device which is attached to or is designed to be attached to an injection device and has a needle holder for attachment purposes with an injection needle projecting in a distal direction. The needle guard device has a lock mechanism, which projects out from the needle holder, likewise in the distal direction, and is spaced radially apart from the injection needle, in other words radially apart from the axis extending from the distal to the proximal end. The lock mechanism comprises a hollow profile, which circumferentially surrounds the injection needle about a longitudinal portion. Also part of the needle guard device is a needle guard, which can be moved radially in the proximal direction between the injection needle and lock mechanism as far as a releasing position which releases the injection needle, and in the distal direction out of the releasing position as far as a guard position, in which it surrounds the injection needle, including the needle tip. The lock mechanism and the needle guard co-operate in a manner which ensures that the needle guard can be locked in the guard position to prevent it from moving in the proximal direction again, i.e. on reaching the guard position it is locked there. The needle guard surrounds the injection needle, thereby reliably preventing access to the injection needle in the guard position. In some embodiments, the needle guard is in the form of a circumferentially extending closed sleeve. In principle, however, it may comprises an opening or openings or orifices, provided it fulfils its guard function in the guard position, i.e. protects the user against injury due to piercing.

In some embodiments of the present invention, the needle guard device also has a locking member disposed radially between the injection needle and the needle guard. The locking member is able to move in the distal direction relative to the injection needle and to the lock mechanism from a proximal position which it assumes in an initial state prior to the injection. The movement in the distal direction is caused by the needle guard when it moves into the guard position after the injection. The needle guard drives the locking member into the guard position. To produce this driving action, the needle guard has a locating element and the locking member has a complementary locating element which move into a driving connection with one another when the needle guard is moved into the releasing position.

In one embodiment, the locating element and the complementary locating element establish the driving connection exactly at the instant at which the needle guard reaches the releasing position. In a second embodiment, the locating element and complementary locating element establish the driving connection before the needle guard has reached the releasing position. In such embodiments, the needle guard device is of the "early triggering" type because the driving connection is established earlier along the distance traveled by the needle guard as the injection needle effects a piercing action than is the case with the first embodiment. In some preferred embodiments, the locating element and the complementary locating element have already established the driving connection during a first half of the distance which the needle guard travels from a distal initial position before reaching the releasing position, and in some preferred embodiments, the locating element and the complementary locating element establish the driving connection in the first third of the distance. The needle guard assumes the distal initial position in an initial state prior to the needle guard device being used. In some embodiments, the driving connection is a catch connection in which the locating element locates behind the complementary locating element by reference to the distal direction. When the needle guard is in the releasing position, the locking member advantageously extends far enough in the distal direction for the injection needle to extend beyond the locking member by only an injection portion which extends into the tissue, e.g. in or through the human skin, during the injection.

Providing a locking member radially between the needle guard and the injection needle imparts additional stiffness to the needle guard in the radial direction. Although the locking member is another element, it nevertheless enables the shape of the needle guard or lock mechanism on the one hand, and that of the needle holder on the other hand, to be simplified. Due to the radially nested arrangement, the molded elements needed for locking the needle guard and establishing the driving connection can be easily produced.

Stiffness can be imparted if the locking member guides the needle guard in a sliding contact during the movement into the releasing position. In some embodiments, the lock mechanism and the locking member form an annular gap between them, in which the needle guard can be guided in a sliding contact on both an internal surface and an external surface respectively. A mechanical return spring may be provided for the needle guard in such an annular gap, and the annular gap also axially guides the return spring. Alternatively, an annular gap may also be provided in the form of a gas-tight annular chamber, the volume of which is reduced or increased due to the movement of the needle guard to generate the elastic force for returning the needle guard in the distal direction by generating an over pressure or negative pressure.

In one embodiment, the locking member is shaped so that it surrounds at least an axial segment of the injection needle, either lying against it or at only a slight distance from it at a distal end or, in some embodiments, across the greater part of its length. It has a thin bore, at least at its distal end and/or across its entire length, which is shaped so that it serves as a locating hole for the injection needle, and the locking member is in sliding contact with the injection needle as it moves in the distal direction. The bore has an extra dimension compared with the external diameter of the injection needle which is no more than is needed to accommodate the latter. As a result, the locking member imparts additional stiffness to the injection needle, which may be 29 to 32G or thinner, to prevent bending.

In some preferred embodiments, when the needle guard is in the guard position, the locking member extends beyond the needle tip in the distal direction. This affords optimum protection against piercing injuries. Furthermore, the extra dimension of the locking member in the distal direction affording the protection and ultimately also that of the needle guard can be minimized as a result, which in turn enables the length of the needle guard device as a whole to be reduced.

In some preferred embodiments, the locating element of the needle guard not only serves to drive the locking member, but, in a dual function, also blocks or locks the needle guard in the guard position. In such embodiments, when the needle guard is in the guard position, the locating elements moves into contact with a lock stop of the lock mechanism in the proximal direction, i.e. a movement of the needle guard in the proximal direction is prevented by the abutting contact of the locating element. To obtain such a lock in the guard position, a radial stiffening of the needle guard by the locking member is advantageous because the locking member affords radial support for the locating element to block a movement of the locating element radially inwardly in the guard position, i.e.

toward the injection needle. As a result, the locating element cannot be inadvertently or deliberately be moved out of the locking engagement with the lock stop.

As the needle guard is moved into the releasing position, the locating element is moved, e.g. radially outwardly, opposing a rebounding elastic force, and is moved into the driving connection by the elastic force. In the driving connection, it assumes a position which is radially farther outward than the position which it assumed in the initial state prior to the injection. The two positions are such that the locating element of some preferred embodiments, in which it causes the needle guard to be locked in the guard position, is able to move past said lock stop of the lock mechanism in the driving connection after the needle guard has moved into the guard position but is still moved reliably in the axial direction into contact with the lock stop of the lock mechanism.

In a preferred embodiment, the lock stop of the lock mechanism can be moved radially outwardly against a rebounding elastic force. In some preferred embodiments, the lock stop may be an elastically flexible lug projecting in the distal direction and having a free distal end, which may be thought of as constituting the lock stop.

In some preferred embodiments, the locking member forms a guide track for the locating element of the needle guard. As the needle guard moves in the proximal direction, i.e. in the direction toward the releasing position, the locating element is moved radially outwardly against a rebounding elastic force until it snaps into the driving connection. The guide track has an inclination with respect to the proximal-distal axis as viewed across its axial extension. The inclination may be continuous, i.e. constantly differentiable. For example, it may be constant or may decrease in the proximal direction or increase in the proximal direction, the biggest increase being in the second proximal half or in the last proximal third of its extension. If, as may be preferred, the locating element is shaped so that it constitutes an elastically flexible lug, this lug should project in the proximal direction, in which case it has a free proximal end.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 1:
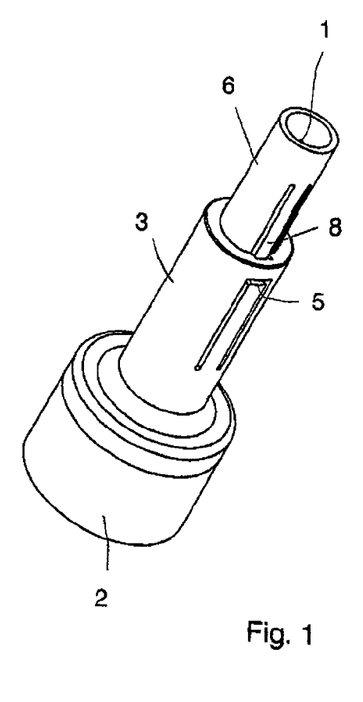
FIG. 1 is a perspective view illustrating a first exemplary embodiment of a needle guard device in accordance with the present invention.

FIG. 1 is a perspective diagram illustrating a needle guard device which can be fitted on the distal end of an injection device. The injection device may be of the type which enables a dose of an injectable product or substance, for example insulin, to be set or selected, and the set dose to be dispensed on a repeated basis. In some such devices, the dose can be re-set with each injection. In some preferred embodiments, the injection device is an injection pen, of the type commonly used for self-administering medicaments, for example for the treatment of diabetes. The injection device is therefore designed for administering several injections, and for a longer service life. The needle guard device which surrounds the injection needle 1 for the injection device, on the other hand, may be designed for a single injection only, i.e. for one-off use only. In readiness for use, it is attached to the distal end of the injection device, for example screwed onto it or, as in the case of the embodiment described as an example, push-fitted or friction fit on it, and removed and disposed of after the injection.

As mentioned above, the needle guard device comprises the injection needle 1, a needle holder 2 and two sleeve-shaped structures, an outer sleeve 3 and an inner sleeve 6, which form a needle guard telescope. The inner sleeve 6 is able to move axially relative to the outer sleeve 3 and relative to the injection needle 1. FIG. 1 illustrates the needle guard device in an initial state in which the inner sleeve 6 assumes a distal (forward) position relative to the outer sleeve 3, in which it covers the injection needle 1 to beyond its needle tip and thus forms a view-blocking guard. The inner sleeve 6 may therefore be thought of and/or referred to as a needle guard 6. The outer sleeve 3 serves to lock the needle guard 6 after the injection and may therefore be thought of and/or referred to herein as a lock mechanism 3.

Figure 2:
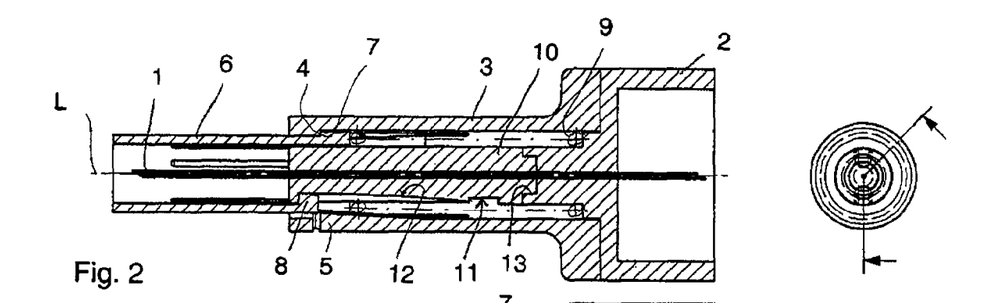
FIG. 2 shows the needle guard device based on the first embodiment in an initial state.

FIG. 2 also illustrates the needle guard device in the initial state. In addition to the longitudinal section, a cross-section of the region of the lock mechanism 3 is also illustrated. The position of the longitudinal section is indicated in the diagram illustrating the cross-section.

The needle holder 2 is in the shape of a cylinder with one closed end or a pot with a base from which a wall extends circumferentially in the proximal direction forming a fixing portion by which the needle holder 2 is attached to the injection device. Projecting out in the distal direction from the central region is a retaining portion for the injection needle 1. The longitudinal axis L of the injection needle 1 coincides with the proximal-distal axis. If, as may be preferred, the injection device conveys the product to be injected by a reciprocating plunger, the axial direction advantageously coincides with the forward-drive or injection direction of the plunger. The injection needle 1 is axially secured to the needle holder 2 in the retaining portion. The injection needle 1 extends through the retaining portion of the needle holder 2. It extends in the proximal direction into a chamber of the fixing portion surrounded by the wall but sits behind a proximal edge of the wall. This chamber is sealed to render it sterile by a film, which is secured to the wall of the needle holder 2 at the proximal end. When the needle guard device is attached to the injection device, the film is destroyed and the proximal pointed end of the injection needle pierces a membrane sealing a distal end of a container filled with the product. As a result, during the process of attaching it to the injection device, a flow connection is simultaneously established between the injection needle 1 and the product container.

Toward its distal end, the injection needle 1 has an injection portion incorporating the needle tip. The length of the injection needle is dimensioned for a subcutaneous injection. Accordingly, the injection portion penetrates the skin and through the skin as far as a subcutaneous injection point. The injection portion extends in the proximal direction from the free needle tip as far as the axial level of the distal end of the lock mechanism 3. In the initial state, the needle guard 6 assumes its distal-most position, which is predefined by the co-operation of a stop 4 of the lock mechanism 3 with a complementary stop 7 of the needle guard 6. The stop 4 is formed by a shoulder projecting radially inward from the lock mechanism 3 and the complementary stop 7 is formed by a shoulder projecting radially outward from the needle guard 6.

The needle guard device also has a return element 9, which is a mechanical compression spring in the embodiment illustrated as an example. The return element 9 exerts an elastic force acting on the needle guard 6 in the distal direction, by which it pushes the complementary stop 7 against the stop 4. The return element 9 is axially supported on the lock mechanism 6 and the needle holder 2.

The needle guard device also has a locking member 10 for the needle guard 6. The locking member 10 extends the retaining portion of the needle holder 2 in the distal direction. It has a cylindrical and, in the embodiment illustrated as an example, circular cylindrical external face, which lies opposite and faces a cylindrical and, in the embodiment illustrated as an example, circular internal face of the lock mechanism 3 disposed parallel at a distance apart. The external face of the locking member 10 and the internal face of the lock mechanism 3 radially bound an axially extending annular gap into which the needle guard 6 is able to move. The return element 9 is also disposed in the annular space. The internal and external surfaces mutually bounding the annular space guide the needle guard 6 during its movement in a sliding contact and also guide the return element 9 as it springs in and out in the embodiment illustrated as an example.

The slide guide formed by the external face of the locking member 10 for the needle guard 6 is interrupted by two guide tracks 12. The guide tracks 12 are formed in the external face of the locking member 10 lying diametrically opposite one another around the injection needle 1. They extend axially lengthways and each has an inclination with respect to the axial. In the longitudinal section illustrated in FIG. 2, only one of the two guide tracks 12 is visible due to the position of the section. The other guide track 12 is the same as the one illustrated in the section. By reference to the axial, the guide track 12 has an inclination which extends radially outwardly and increases in the proximal direction.

The needle guard 6 has two locating elements 8, each of which co-operates with one of the guide tracks 12. In the section illustrated in FIG. 2, only one of the locating elements 8 is visible. The other locating element 8 is of the same shape as the one illustrated and also the same in terms of the way it co-operates with the other guide track 12. The locating element 8 is provided in the form of a flexibly elastic lug extending out in the proximal direction from a root region in the casing of the needle guard 6 and has a shoulder projecting radially inward at its proximal end. The shoulder results in an inwardly projecting cam on the proximal end of the locating element 8. This cam is in a sliding contact with the guide track 12. When the needle guard 6 moves in the proximal (rearward) direction, the cam slides on the guide track 12 so that the locating element 8 is gradually bent elastically outwardly to an increasing degree due to the inclined contour or slope of the guide track 12. A recess is formed in the external face of the locking member 10 at the proximal end of the guide track 12, which serves as a complementary locating element 11. The transition between the guide track 12 and the complementary element 11 is abrupt, i.e. the guide track 12 phases out or transitions steeply at its end into the recess acting as the complementary locating element 11. The same applies to the guide track 12 on the oppositely lying side not illustrated in FIG. 2, i.e. where another complementary locating element 11 is provided. When the locating element 8 is in the illustrated distal initial position already lying on the guide track 12, it also ensures that the locking member is retained.

The locking member 10 is connected to the needle holder 2 sufficiently securely to prevent it from leaving the position illustrated in FIG. 2 due to accelerations, for example if subjected to vibrations or impact, such as will normally occur during transportation or handling. However, the connection is releasable. The connection is established by a friction contact between the needle holder 2, its retaining portion, and the locking member 10. At its proximal end, the locking member 10 rests in or against a mount formed on the distal end of the retaining portion of the needle holder 2 by a firm frictional contact. The seating surfaces co-operating to produce this frictional contact are the internal face of the mount of the needle holder 2 and a matching friction contact surface 13 of the locking member 10. The friction contact surface 13 is the external face of a base extending out from the proximal end face of the locking member 10 in the proximal direction. The friction contact surface 13 tapers, e.g. conically, in the proximal direction, and the shape of the friction contact surface of the needle holder 2 is adapted accordingly.

When the friction contact connection is released, the locking member 10 slides in the distal direction relative to the injection needle 1. The injection needle 1 extends through the locking member 10, which has a bore designed to accommodate the external diameter of the injection needle 1 for this purpose. The locking member 10 therefore surrounds the injection needle 1, sitting tightly around it, and thus helps to prevent bending deformations as far as its distal end. However, there should be only the smallest possible amount of friction when the locking member 10 slides relative to the injection needle 1. The locking member 10 may, therefore, advantageously made from a material with a low coefficient of friction, for example a plastic material.

The locking member 10 as a whole has the shape of a slim bolt. It imparts stiffness to the needle guard 6 and to its locating elements 8 with respect to the radial direction.

The lock mechanism 3 is fixedly connected to the needle holder 2 in a proximal end portion. For the lock mechanism 3 to fulfil its function in terms of protecting against accidental contact with the injection needle 1, the lock mechanism 3 could be made in a single piece with the needle holder 2. As regards assembling the needle guard device, however, it may be of advantage to manufacture it separately from the needle holder 2.

One function of the lock mechanism 3 is to establish a locking connection with the needle guard 6 to prevent it from moving in the proximal direction when it is disposed in a distal guard position. In the guard position, the needle guard 6 assumes the same position by reference to the axis L as it does in the initial position illustrated in FIG. 2. However, when the needle guard 6 is in the guard position, it is prevented from moving in the proximal direction, and is so by the lock mechanism 3. To enable it to fulfil the locking function, the lock mechanism 3 has two locking elements 5. The locking elements 5 are respectively provided in the form of a flexibly elastic lug. The locking elements 5 are disposed in the sleeve casing of the lock mechanism 3, each extending out in the distal direction from a proximal root or base region. The locking elements 5 each have a distal free end, therefore. The distal end faces of the locking elements 5 acts as stop surfaces for the proximal end faces of the locating elements 8 lying axially opposite when the needle guard 6 is in the guard position. The locking elements 5 therefore respectively act as a lock stop and the locating elements 8 respectively act as a lock complementary stop in order to lock the needle guard 6 in the guard position. In the guard position, the needle guard 6 surrounds the injection portion of the injection needle 1 to beyond its needle tip.

In the initial state illustrated in FIG. 2, the lock stop of the locking element 5 and the complementary lock stop of the locating element 8 are not engaged. The locating element 8 sits at least essentially free of tension on the distal end of the guide track 12. From this position, it can be moved radially inwardly past the locking element 5 unhindered as the needle guard 6 is moved in. The same applies to the pair comprising the locking element 5 and locating element 8 offset by 180° in the circumferential direction. Although the needle guard device may have several pairs of co-operating elements 5 and 8 and these may be advantageously disposed in a symmetrical arrangement about the axis L, a single pair of elements 5, 8 is enough to establish the lock.

A description will be given below with reference to FIGS. 2 to 4 to explain the sequence which takes place during an injection.

Once the user has attached the needle guard device to the injection device as described above, the injection needle 1 is primed. The user then selects the dose to be injected. Having selected the dose, he places the injection device on the desired injection point of the skin by the distal end face of the needle guard 6 and pushes the injection device against the skin. Due to this pressing action in the distal direction, the needle guard 6 moves axially against the elastic force of the return element 9 through the annular gap between the lock mechanism 3 and the locking member 10. The needle guard 6 is axially guided relative to the lock mechanism 3 but is not able to rotate. In what is the first distal portion of the movement, the locating elements 8 slide along the respective co-operating guide track 12. The guide tracks 12 are either axially straight or only very slightly outwardly inclined at their distal end portions so that the locating elements 8 are able to move radially inward past the respective co-operating lock element 5 without any difficulty. During the next part of the movement, the locating elements 8 are bent elastically outwardly along the radially widening guide tracks 12. The lock mechanism 3 becomes wider in the circumferential region of its locking elements 5 in the proximal direction to the degree that the locating elements 8 are able to bend outwardly virtually unhindered, e.g. without the locking elements 5 deforming. At the proximal ends of the guide tracks 12, the locating elements 8 move across the edges distally bounding the complementary locating elements 11 at this point and inward due to their natural rebounding elastic force; they therefore snap into the complementary locating elements 11. The locating elements 8 and complementary locating elements 11 are now hooked to one another in pairs in a driving connection.

As explained above, the internal face of the locking element 5 facing the guide track 12 is shaped so that a sufficiently large distance is left free between the internal face and the guide track 12 across the entire stroke of the needle guard 6 so that the locating element 8 does not exert any pressure on the locking element 5 or at least any outwardly directed pressure on the locking element 5. The complementary element 11 and the guide track are also shaped so that in the initial position, the locating element 8 is bent outwardly from its distal initial position in the driving connection and is therefore at a greater distance from the central longitudinal axis L in the driving connection than in the distal initial position. During the movement into the releasing position, the locating elements 8 therefore sit deeper in the respective co-operating guide track 12 than they do when being moved out of it. In the driving connection, an external face of the locating element 8 facing the locking element 5 is at a greater distance from the central longitudinal axis L than the locking element 5 on its internal face in the distal region.

Figure 3:
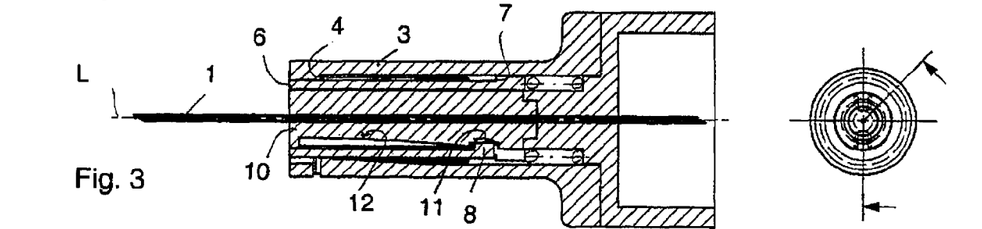
FIG. 3 illustrates the needle guard device based on the first embodiment, with the needle guard in the releasing position.

FIG. 3 illustrates the needle guard device with the locating elements 8 and complementary locating elements 11 in the driving connection. The driving connection prevents any further movement of the needle guard 6 in the proximal direction. Furthermore, the needle guard 6 has been moved by its entire length into the axial overlap with the lock mechanism 3. In this fully retracted state, the distal ends of the lock mechanism 3, needle guard 6 and locking member 10 are disposed on the same axial level. The injection needle 1 extends by its entire injection portion beyond these common ends, i.e. the injection needle 1 has penetrated the skin and subcutaneous tissue lying underneath by the desired penetration depth of the injection needle 1 as measured along the injection needle 1, and the set dose can be dispensed. During dispensing, it is necessary to apply only the pressure needed to overcome the rebounding elastic force of the return element 9. Once the set dose has been dispensed, the user moves the injection device axially away from the injection point in the proximal direction so that the needle guard 6 is relieved of pressure. The needle guard 6 therefore moves back out axially in the distal direction again under the effect of the return element 9 and back into its distal position defined by the co-operating stop 4 and complementary stop 7.

Figure 4:
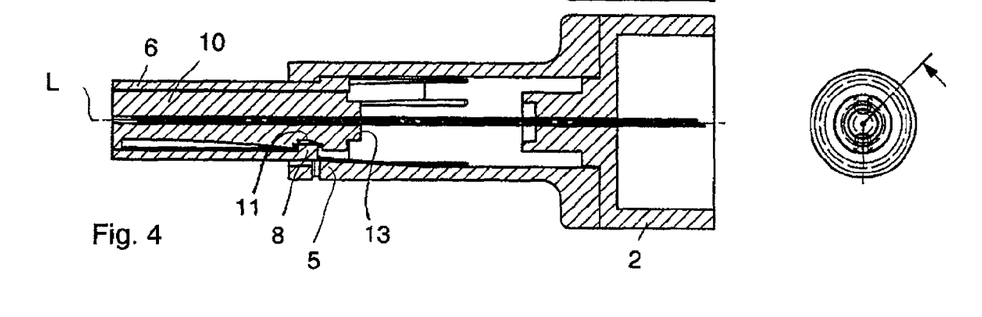
FIG. 4 illustrates the needle guard device based on the first embodiment, with the needle guard in the guard position.

FIG. 4 illustrates the needle guard device after the injection, with the needle guard 6 in the distal-most position. At the end of the movement of the needle guard 6 in the distal direction, the needle guard device automatically locks via the co-operating locating elements 8 and locking elements 5 so that the distal-most position is now the locked guard position of the needle guard 6. During the movement in the distal direction, the needle guard 6 drives the locking member 10 with it in the proximal direction due to the driving connection of elements 5, 8. Since the locating elements 8 are also still bent radially outwardly in driving connection and the locking elements 5 are inwardly inclined in the distal direction at their internal faces directed towards the locating elements 8, the locating elements 8 move into sliding contact with the internal face of the respective co-operating locking element 5 during the extraction movement so that the locking elements 5 are bent elastically outwardly. At the end of the movement in the distal direction, the locating elements 8 move so that their proximal end faces lie in front of the locking elements 5 so that the locking elements 5 snap inwardly due to their natural rebounding elastic force and act as a lock stop for the respective co-operating locating element 8. The needle guard 6 is locked in the guard position as a result.

The locking member 10 supports the locating elements 8 radially inwardly so that they can not be moved out of the lock connection with the locking elements 5. The locking elements 5, locating elements 8 and guide tracks 12 are advantageously shaped so that the locking elements 5 are elastically biased in the distal direction to a relevant degree only during the movement of the needle guard 6. The locating elements 8 which bend outwardly during the retracting movement should at most cause the locking elements 5 to bend to a significantly lesser degree. The locking elements 5 may not be biased at all during the retracting movement. In the embodiment illustrated as an example, this is achieved due to the inclined contour of the internal faces of the locking elements 5 and guide tracks 12 as viewed in the longitudinal section and the slim locating elements 8.

The complementary locating elements 11 are disposed with respect to the axial direction so that they are axially overlapped by the lock mechanism 3 when the needle guard 6 is in the guard position, so that the lock mechanism 3 prevents manipulations of the locating elements 8 which could cause the locating elements 8 to move out of the driving connection.

As also illustrated in FIG. 4, the locking member 10 with its bore designed to accommodate the injection needle 1 offers reliable protection against injuries by piercing. The needle tip sits in the bore positioned at a short distance back from the mouth of the bore. It is therefore no longer possible to inadvertently touch the injection needle 1 in the guard position.

After the injection, the user removes the needle guard device from the injection device and disposes of it. For a new injection, a new needle guard device in the initial state illustrated in FIG. 2 is attached to the injection device.

Figure 5:
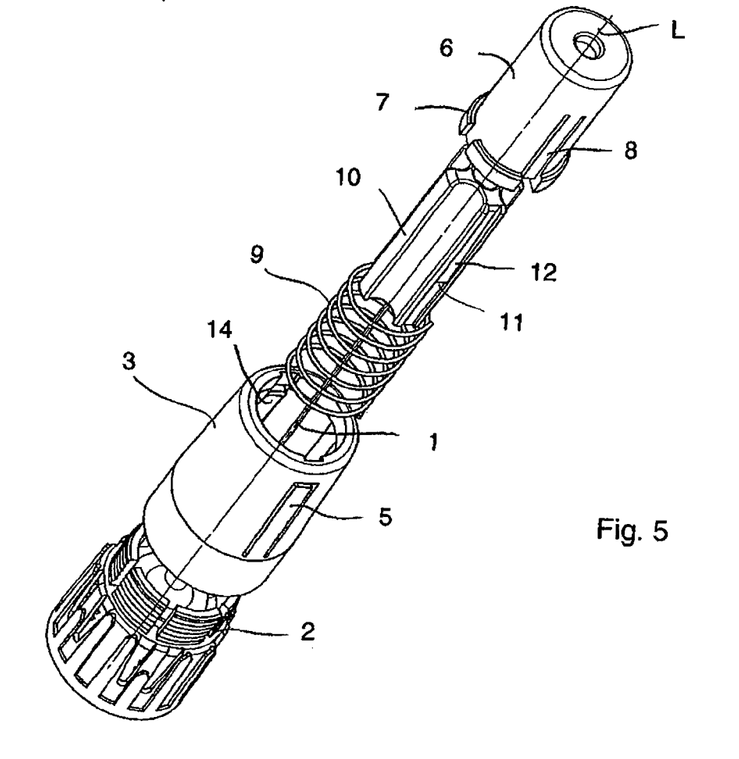
FIG. 5 is an exploded diagram illustrating a second exemplary embodiment of a needle guard device in accordance with the present invention.
Figure 6:
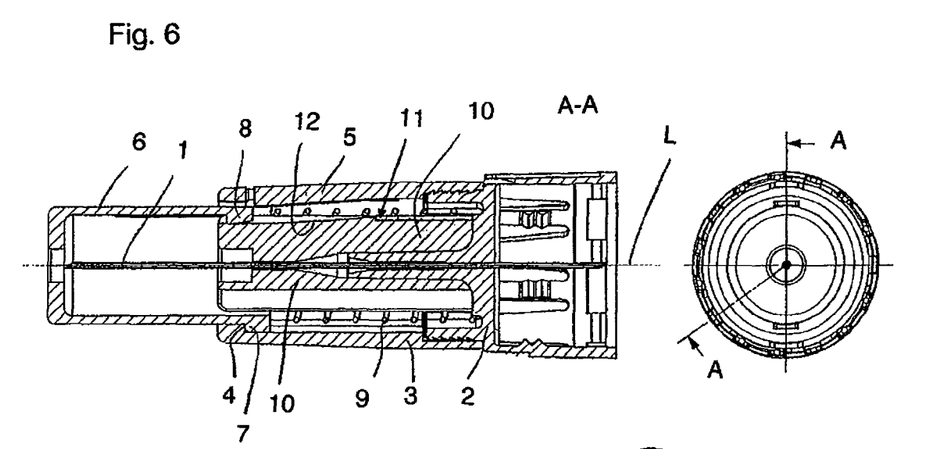
FIG. 6 shows the needle guard device of FIG. 5 in an initial state.

FIGS. 5 and 6 illustrate a needle guard device of a second embodiment of the present invention. The needle guard device differs from the needle guard device based on the first embodiment essentially due to the fact that, as viewed in cross-section, several axially extending ribs are provided on the locking member 10 extending out from a central region in the second embodiment. The locking member 10 has four such ribs, which are offset from one another by 90° in the circumferential direction, thus resulting overall in a cross shape when viewed in cross-section. The ribs respectively extend as far as the internal face of the needle guard 6. Formed on the external face of two of the ribs in each case is one of the guide tracks 12 and a complementary locating element 11 is provided in each case at the proximal end of the guide track 12. The way in which the locating elements 8 co-operate with the guide tracks 12 and complementary elements 11 corresponds to that of the first embodiment, i.e. the driving connection is not established until the releasing position is reached. In this respect, the needle guard devices based on the first and second embodiment are "late-releasing" designs. FIG. 5 also illustrates the locating mechanism which guide the needle guard 6 relative to the lock mechanism 3 and prevent it from rotating. The guiding action is achieved due to the complementary stops 7 locating with axial guides 14 formed on the internal surface of the lock mechanism 3.

Figures 7, 8:
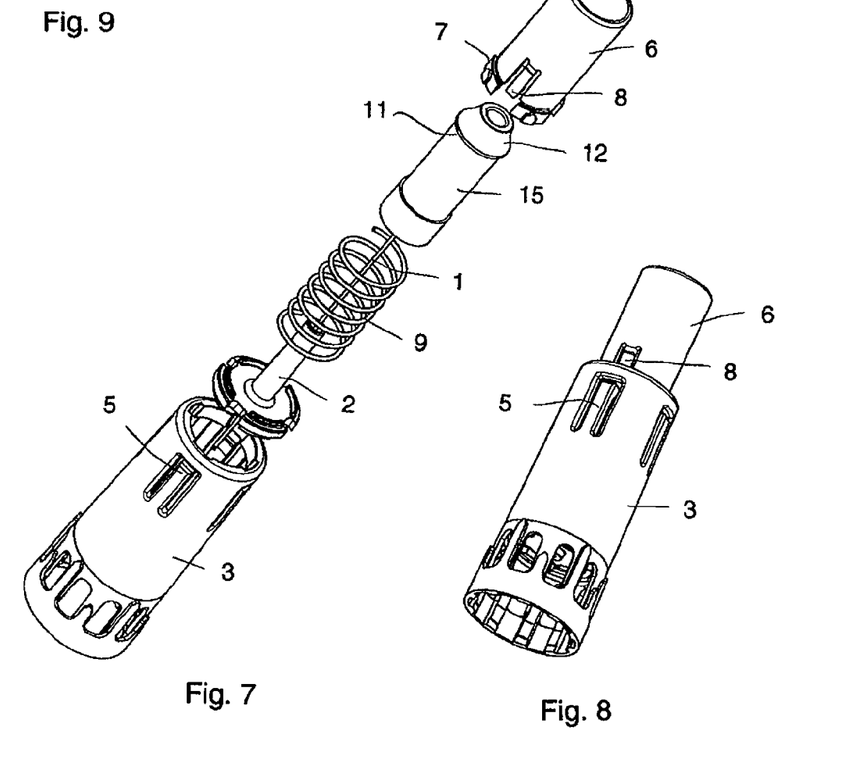
FIG. 7 is an exploded diagram showing another exemplary embodiment of a needle guard device in accordance with the present invention.
FIG. 8 is a perspective view showing the needle guard device of FIG. 7 in the assembled state.

FIG. 7 is an exploded diagram illustrating a needle guard device of another embodiment of the present invention, with the components of the needle guard device shown individually along the central longitudinal axis L. The depicted needle guard device is of an "early-triggering" design and has a locking member 15 which is modified in terms of how it co-operates with the guide track 12 and the complementary locating element 11 to achieve early triggering. Another difference is the design of the needle holder 2 and the lock mechanism 3. The needle holder 2 is inserted in the sleeve-shaped lock mechanism 3 and the lock mechanism 3 serves as the fixing portion for attaching the needle guard device to an injection needle. As may be seen from FIG. 9, the needle holder 2 is inserted in the lock mechanism 3 and in the inserted state is connected to the lock mechanism 3 so that it is not able to move axially or rotate about the longitudinal axis L.

Figure 9:
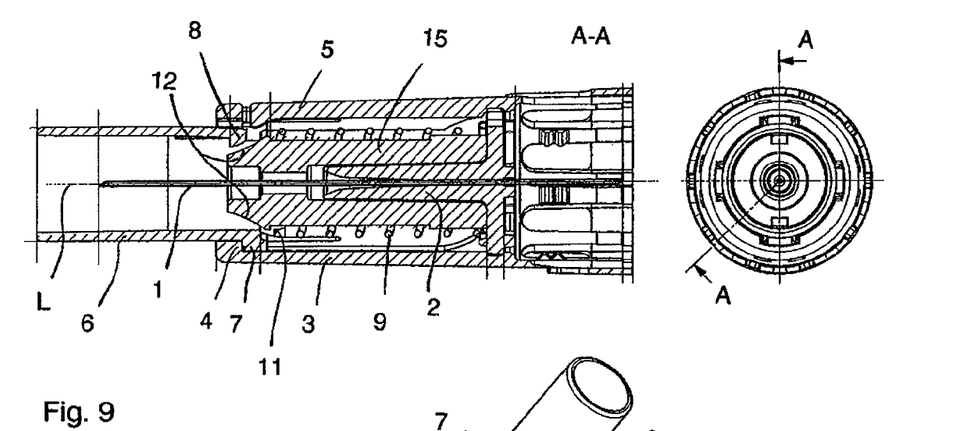
FIG. 9 shows the needle guard of FIG. 7 in an initial state.

FIG. 8 illustrates the needle guard device once the individual components illustrated in FIG. 7 have been assembled, with the needle guard 6 in the distal initial position, and FIG. 9 illustrates the needle guard device in a cross-section and a longitudinal section A-A indicated in the cross-section.

To achieve early triggering, the shoulder serving as the complementary locating element 11 which is hooked by the locating element 8 in the driving connection is disposed in a distal end portion of the locking member 15. The guide track 12 disposed distally in front of the complementary locating element 11 is shorter in terms of the position of the complementary locating element 11 than is the case with the guide tracks of the other embodiments. It also has a more pronounced inclination with respect to the longitudinal axis L than the guide tracks 12 of the other embodiments. An external circumferential surface of the locking member 15 extending circumferentially about the longitudinal axis L forms the guide track 12 for each of the locating elements 8, and the needle guard 6 has two locating elements 8. At the distal end of the guide track, the locking member 12 merges radially inwardly into a steep shoulder which likewise extends circumferentially about the longitudinal axis L. The shoulder serves as the complementary element 11 for each of the locating elements 8.

A description will be given below of the components of the needle guard device used to achieve early triggering and how they operate. Reference will also be made to the descriptions of the other embodiments. In particular, where components of the embodiments fulfil the same function, the same reference numbers will be used.

The way in which the needle guard device based on the third exemplary embodiment works will be explained with reference to FIGS. 10 to 13 and the early triggering mechanism will be explained.

Figures 10, 11:
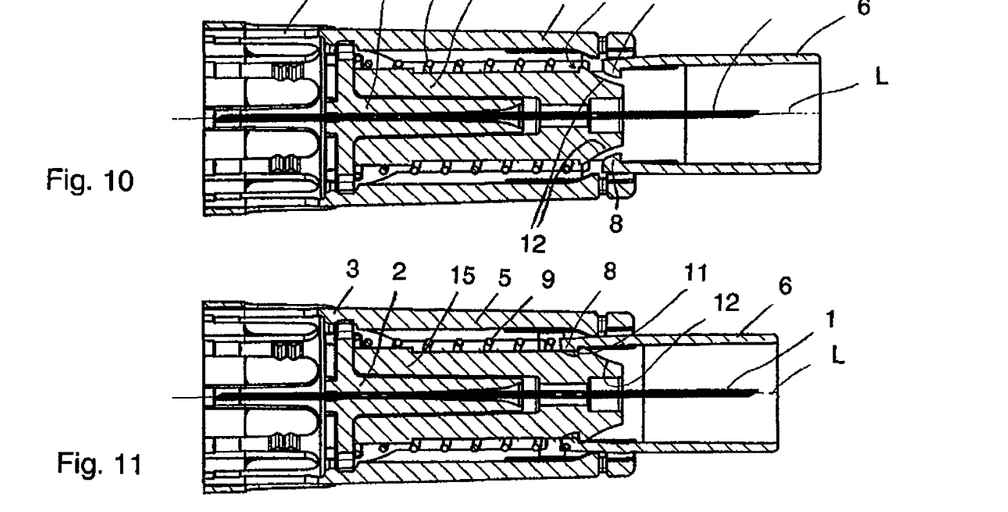
FIG. 10 is a longitudinal section different from that of FIG. 9, showing the needle guard device in the initial state.
FIG. 11 shows the needle guard device of FIG. 7, with the needle guard in a releasing position.

FIG. 10 illustrates the needle guard device in an initial state prior to use, in which the needle guard 6 assumes the distal initial position. In the initial position, the needle guard 6 is held on the lock mechanism 3 by the co-operating stops 4 and 7 (FIG. 9), as in the other embodiments. The two locating elements 8 lie distally immediately in front of the guide track 12 and are relaxed. When an axial pressure is applied to the needle guard 6 in the proximal direction, the needle guard 6 moves in the proximal direction relative to the lock mechanism 3 and relative to the locking member 15 disposed in its proximal initial position. Coinciding with the start of the movement, the locating elements 8 move into guide contact with the guide track 12 and bend radially outwardly, conforming to the inclination of the guide track 12. The locating elements 8 move along the guide track 12 in the gap between the locking member 15 and the locking elements 5 and are bent radially outwardly to a constantly increasing degree until reaching the proximal end of the guide track 12 and snap radially inward behind the complementary locating element 11 due to their elastic rebounding force, thereby establishing the driving connection.

FIG. 11 illustrates the needle guard device with the needle guard 6 in the trigger position, i.e. with the needle guard 6 in the driving connection. Due to the fact that the complementary element 11 is in a position pushed further forward in the distal direction than is the case in the other two embodiments, the driving connection has already been established before the tip of the injection needle 1 extends out beyond the needle guard 6 in the distal direction. In the embodiment illustrated as an example, the needle tip is still positioned at some distance back from the needle guard 6. Further pressure applied to the needle guard 6 causes the needle guard 6 to move further into the lock mechanism 3 against the force of the return element 9. During this additional inward movement, the locating elements 8 move across the axially straight, in this embodiment circular cylindrical, circumferential surface adjoining the complementary element 11, in the proximal direction.

Figure 12:
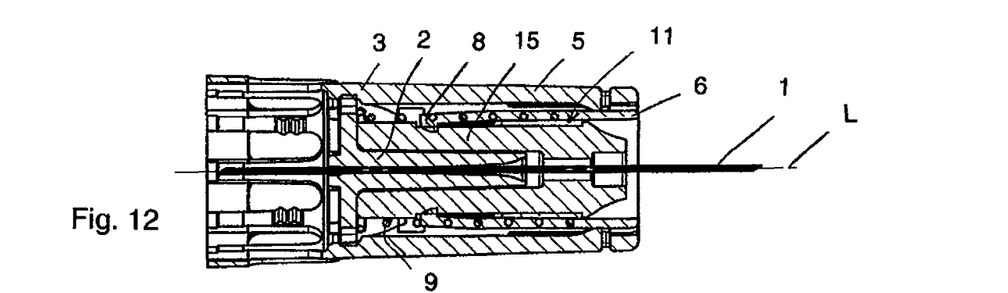
FIG. 12 shows the needle guard device of FIG. 7, with the needle guard in a trigger position.

FIG. 12 illustrates the needle guard device with the needle guard 6 disposed in the releasing position. Axial pressure on the needle guard 6 causes the needle guard 6 to remain in the releasing position against the force of the return element 9. When the needle guard 6 is relieved of axial pressure, the needle guard 6 automatically moves forward in the distal direction again due to the rebounding force of the return element 9 until the locating elements 8 move into an abutting contact with the complementary element 11. The distance of the complementary element 11 from the contact surface of the needle holder 2 in the initial position (FIG. 10) is dimensioned so that the locking member 15 is driven in the distal direction with the needle guard 6 in the driving connection now re-established between the locating elements 8 and the complementary element 11. Across the distance of the joint movement of the needle guard 6 and locking member 15, the locating elements 8 move in the distal direction in front of the locking elements 5 of the lock mechanism 3. As with the other two embodiments, the locating elements 8, i.e. the ends thereof which locate, are disposed radially farther out than when the needle guard is in the initial position. During the outward movement, the locking elements 5 are therefore bent radially outwardly and snap back radially inward due to their natural elastic rebounding force as soon as they have moved past the locating elements 8.

Figure 13:
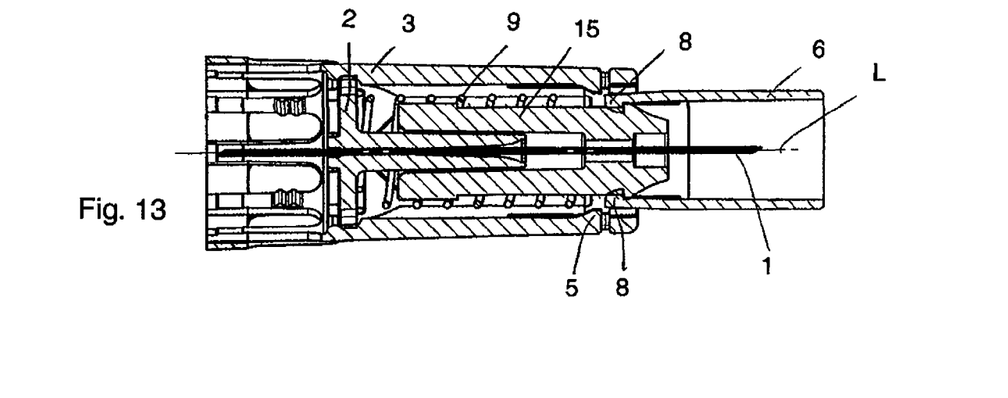
FIG. 13 shows the needle guard device of FIG. 7, with the needle guard in the guard position.

FIG. 13 illustrates the needle guard device based on the third embodiment in the guard position, in which the locking elements 5 have snapped proximally in front of the locating elements 8 co-operating in the driving connection and act as lock stops for the locating elements 8 and hence for the needle guard 6.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A needle guard for an injection device, the needle guard comprising:
   a) an injection needle,
   b) a needle holder which is attached to or can be attached to the injection device, from which the injection needle extends in a distal injection direction,
   c) a lock mechanism which extends out from the needle holder and is spaced radially apart from the injection needle,
   d) a needle guard member arranged radially between the injection needle and the lock mechanism, which can be moved in a proximal direction opposite the distal injection direction as far as a releasing position in which the injection needle projects from the needle guard and out of the releasing position in the distal injection direction as far as a guard position in which the needle guard member surrounds the injection needle, including a needle tip, and which can be locked in the guard position by the lock mechanism to prevent another movement in the proximal direction, and
   g) a locking member arranged radially between the injection needle and the needle guard member and able to move relative to the injection needle from a proximal position in the distal injection direction, wherein
   h) the needle guard member has a locating element and the locking member has a complementary locating element, wherein the locating element and the complementary locating element move into a driving connection with one another when the needle guard member is moved into the releasing position, and the needle guard member drives the locking member in the distal injection direction by the driving connection during the movement into the guard position, and wherein
   i) in the guard position of the needle guard member, the locking member is arranged in a position that supports the locating element radially inwardly and prevents the needle guard member from moving out of a locked connection with the lock mechanism by blocking a radial inward movement of the locating element.

2. The needle guard as claimed in claim 1, wherein the locking member guides the needle guard member in a sliding contact.

3. The needle guard as claimed in claim 1, wherein the locking member surrounds the injection needle at one of a slight radial distance apart from it, at least at its distal end, or in a sliding contact.

4. The needle guard as claimed in claim 1, wherein the locking mechanism comprises a lock stop and, when the needle guard member is in the guard position, the locating element moves in the proximal direction into contact with the lock stop.

5. The needle guard as claimed in claim 4, wherein the lock stop can be moved radially outwardly against an elastic force as the needle guard member moves into the guard position.

6. The needle guard as claimed in claim 4, wherein a first flexibly elastic lug extending in the longitudinal direction of the injection needle constitutes the lock stop and a second flexibly elastic lug extending in the longitudinal direction of the injection needle constitutes the locating element.

7. The needle guard as claimed in claim 6, wherein the first lug has a free distal end and the second lug has a free proximal end.

8. The needle guard as claimed in claim 1, wherein the locating element is able to move radially outwardly against an elastic force.

9. The needle guard as claimed in claim 1, wherein the locking member has a guide track for the locating element, which extends in the proximal direction with an inclination radially outwardly to deflect the locating element radially outwardly during the movement into the releasing position.

10. The needle guard as claimed in claim 9, wherein the guide track is phased out radially inwardly at a proximal end to form the complementary locating element.

11. The needle guard as claimed in claim 9, wherein the guide track is shaped, by reference to a longitudinal axis of the injection needle, with an inclination such that the locating element and the complementary locating element move into the driving connection before the needle guard member has reached the releasing position.

12. The needle guard as claimed in claim 11, wherein the locating element and the complementary locating element move into the driving connection in a first half of the distance traveled by the needle guard member from a distal initial position defined by a stop to the releasing position.

13. The needle guard as claimed in claim 1, further comprising a return element which exerts an elastic force on the needle guard member in the distal direction.

14. A needle protector comprising a needle holder for operable coupling to an injection device and from which a needle projects, a lock which projects from the needle holder and is radially distanced from the needle, a needle cover which can be moved into a first position and, from the first position, to a protecting position in which it surrounds the needle, and which can be prevented from leaving the protecting position by the lock, and a safety member arranged between the needle and the needle cover such that it can be displaced toward a dispensing end of the needle, wherein the needle cover comprises an engagement element and the safety member comprises a counter-element, the engagement element and counter-element mutually engaging when the needle cover is moved into the first position, the needle cover thereby entraining the safety member toward the dispensing end of the needle during movement of the needle cover to the protecting position, wherein in the protecting position of the needle cover, the safety member is arranged in a position that supports the engagement element radially inwardly and prevents the needle cover from moving out of a locked connection with the lock by blocking a radial inward movement of the engagement element.

15. A needle guard for an injection device, the needle guard comprising:
an injection needle,
a needle holder which is attached to or can be attached to the injection device, from which the injection needle extends in a distal injection direction,
a lock mechanism which extends out from the needle holder and is spaced radially apart from the injection needle;
a needle guard member arranged radially between the injection needle and the lock mechanism, the needle guard member being radially surrounded by the lock mechanism along at least a portion of its length, wherein the needle guard moves in a proximal direction as far as a releasing position in which the injection needle projects from the needle guard and out of the releasing position in the distal injection direction as far as a guard position in which the needle guard member surrounds the injection needle, including a needle tip, and which is locked in the guard position by the lock mechanism to prevent another movement in the proximal direction, and
a locking member arranged radially between the injection needle and the needle guard member and able to move relative to the injection needle from a proximal position in the distal injection direction, wherein
the needle guard member has a locating element and the locking member has a complementary locating element, wherein the locating element and the complementary locating element move into a driving connection with one another when the needle guard member is moved into the releasing position, and the needle guard member drives the locking member distally by the driving connection during the movement of the needle guard member into the guard position, and wherein
in the guard position of the needle guard member, the locking member is arranged in a position that supports the locating element radially inwardly and prevents the needle guard member from moving out of a locked connection with the lock mechanism by blocking a radial inward movement of the locating element.

16. The needle guard as claimed in claim 15, wherein the driving connection is configured such that during the movement of the needle guard member into the guard position, the needle guard member and the locking member are driven as a unit in the distal direction relative to the injection needle.

17. The needle guard as claimed in claim 15, wherein the locked connection between the needle guard member and the locking mechanism comprises an abutting contact of a proximal surface of the needle guard member with a distal surface of the lock mechanism.

18. The needle guard as claimed in claim 15, wherein the lock mechanism is configured such that the lock mechanism acts as a lock stop and the locating element acts as a complementary lock stop to lock the needle guard member in the guard position.

* * * * *